US005610063A

United States Patent [19]
Smith et al.

[11] Patent Number: 5,610,063
[45] Date of Patent: Mar. 11, 1997

[54] **CDNA FOR α-N-ACETYL-GALACTOSAMINIDASE FROM *GALLUS DOMESTICUS***

[75] Inventors: Daniel S. Smith; John C. Walker, both of Columbia, Mo.

[73] Assignee: Curators of the University of Missouri, Columbia, Mo.

[21] Appl. No.: 406,070

[22] Filed: Mar. 17, 1995

Related U.S. Application Data

[63] Continuation-in-part of Ser. No. 135,920, Oct. 13, 1993, abandoned.

[51] Int. Cl.$^6$ .............................. C12N 15/56; C12N 15/81
[52] U.S. Cl. .............................. 435/254.23; 435/252.3; 435/252.33; 435/320.1; 435/200; 435/201; 536/23.2
[58] Field of Search .............................. 435/200, 201, 435/320.1, 252.3, 252.33, 254.23; 536/23.2

[56] References Cited

U.S. PATENT DOCUMENTS

| | | | |
|---|---|---|---|
| 4,330,619 | 5/1982 | Goldstein | 435/2 |
| 4,427,777 | 1/1984 | Goldstein | 435/240 |
| 4,609,627 | 9/1986 | Goldstein | 435/269 |

OTHER PUBLICATIONS

Watanabe, K. et al., Status of Blood Group Carbohydrate Chains . . . , J. Exp. Med. 144, 644–653 (1976).
Mollison, Chapter 6: Red Cell Antigens and Antibodies . . . , Blood Transfusion in Clinical Medicine, pp. 194–266, Blackwell Scientific Publications, London, England (1987).
Dahr, Recent Advances in Blood Group Biochemistry, American Association of Blood Banks, Arlington, Virginia, pp. 23–50 (1986).
Uhlenbruck, et al. Allergie Klin. Immunol. 138, 423 (1969).
Tsuji, et al. Molecular Cloning of a Full–Length cDNA for Human α–N–Acetylgalactosaminidase, Biochem. Biophys. Res. Commun. 163:1498–1509 (1989).
Koide, et al. A Case of Fabry's Disease in a Patient with no α–galactosidase A Activity . . . , FEBS Lett. 259:353–356 (1990).
Sumner–Smith, et al. Analysis of the inducible MEL1 gene of *Saccharomyces carlsbergensis* . . . , Gene 36:333–340 (1985).
Overbeeke, et al. "Cloning and Nucleotide Sequence of the α–galactosidase cDNA from Cyamopsis Tetragonoloba (guar)", *Plant Mol. Bio.* 13:541–550 (1989).
Harmening, Modern Blood Banking and Transfusion Practices, F. A. Davis, Philadelphia, PA, p. 212 (1989).
Harpaz, et al., α–Galactosidase, Meth. Enzymol. 33:347–350 (1974).
Smith, et al., Measurement of Protein Using Bicinchoninic Acid, Anal. Biochem., 150:76–85 (1985).
Dean, et al., Fabry Disease, Practical Enzymology of the Sphingolipidoses, Alan R. Lise, Inc., NY, (1977), pp. 173–216.
Laemmli, U.K., Cleavage of Structural Proteins during the Assembly of the Head of Bacteriophage T4, Nature, 227:680–685 (1970).
Moore, et al., A Modified Ninhydrin Reagent for the Photometric Determination of Amino Acids and Related Compounds, J. Biol. Chem., 211:907–913 (1954).
Macfarlane, et al. "Contribution of the Microflora to Proteolysis in the Human Large Intestine", *J. Appl. Bacteriol.* 64:37–46 (1988).
Twining, S. Fluorescein Isothiocyanate–Labeled Casein Assay for Proteolytic Enzymes, Anal. Biochem. 143:30–34 (1984).
Bryant, N. An Introduction to Immunohematology, Immunohematology, W.B. Saunders, Philadelphia, PA pp. 280–297 (1982).
Sung–Sang, et al. Purification and Partial Characterization of Porcine Liver α–N–Acetylgalactosaminidase, J. Biol. Chem., 255:6589–6594 (1980).
Dean, et al. Purification and Enzymatic Properties of α–Galactosidase B (α–N–Acetylgalactosaminidase), J. Biol. Chem. 254:10001–10005 (1979).
Uda, et al. α–N–Acetylgalactosaminidase from the Limpet, Patella Vulgata, J. Biol. Chem. 252:5194–5200 (1977).
Dean, et al. The Identification of α–Galactosidase B From Human Liver As An α–N–Acetylgalactosaminidase, Biochem. Biophys. Res. Commun. 77:1411–1417 (1977).
Schram, et al. The Identity of α–Galactosidase B From Human Liver, Biochim. Biophys. Acta 482:138–144 (1977).
Kusiak, et al. Purification and Properties of the Two Major Isozymes of α–Galactosidase from Human Placenta, J. Biol. Chem., 253:184–190 (1978).
Wang, et al. Human α–N–Acetylgalactosaminidase–Molecular Cloning, Nucleotide Sequence, and Expression of a Full–length cDNA, J. Biol. Chem. 265:21859–21866 (1990).

(List continued on next page.)

*Primary Examiner*—Charles L. Patterson, Jr.
*Assistant Examiner*—Keith D. Hendricks
*Attorney, Agent, or Firm*—Kohn & Associates

[57] ABSTRACT

A purified and isolated cDNA clone, as set forth in SEQ ID No:1, encoding the mature chicken α-N-acetylgalactosaminidase enzyme is disclosed.

5 Claims, 5 Drawing Sheets

OTHER PUBLICATIONS

Sandhu, et al. Dual Asymmetric PCR: One–Step Construction of Synthetic Genes, Biotechniques 12:14–16 (1992).

Sambrook, et al. Molecular Cloning: A Laboratory Manual, 2nd Ed. pp. 6.46–6.48, 8.46–8.51, Cold Spring Harbor Lab., Cold Spring Harbor (1989).

Feinberg, et al. A Technique for Radiolabeling DNA Restriction Endonuclease Fragments to High Specific Activity, Anal. Biochem. 132:6–12 (1983).

Walker, J. C. Receptor–like Protein Kinase Genes *Arabidopsis thaliana*, The Plant Journal, 3:451–456 (1993).

Goldstein, et al. Group B Erythrocytes Enzymatically Converted . . . , Science 215:168–170 (1982).

Hata et al. Purification and Characterization of N–acteyl–α–. . . , Biochem. Intl. 28:77–86 (1992).

Goldstein, "Conversion of ABO Blood Groups", J.Trans. Med. Reviews 3:206–212 (1989).

McGuire, et al. β–N–Acetylglucosaminidase, α–N–Acetylgalactos . . . , Meth. Enzymol. 28:755–763 (1972).

McDonald, et al. α–N–Acetylgalactosaminidase from Aspergillus . . . , Meth. Enzymol. 28:735–738 (1972).

Kadowaki, et al. Isolation and Characterization of a Blood Group . . . , Agri. Biol. Chem. 53:111–120 (1989).

Weissmann, et al. Mammalian α–Acetylgalactosaminidase . . . , Biochem. 8:2034–2043 (1969).

Itoh, et al. α–N–Acetygalactosaminidase from Squid Liver . . . , J. Biochem. 95:959–970 (1984).

Nakagawa, et al. Purification and Characterization of α–N–Acetygalactosaminidase from Skipjack Liver, J. Biochem., 101:855–862 (1987).

Kubo, S. Changes in the Specificity of Blood Groups Induced by Enzymes from Soil Fungi, J. Forensic Sci. 34:96–104 (1989).

Weissmann, B. α–Acetygalactosaminidase from Beef Liver, Meth. in Enzymol. 28:801–805 (1972).

Goldstein, J. "Preparation of Transfusable Red Cells by Enzymatic Conversion", *The Red Cell*, 6th Ann Arbor Conf., 139–157 (1984).

Issitt, Applied Blood Group Serology, Montgomery Scientific Publications, Miami, Florida, pp. 173–178; 194–196; and 209–214.

Henikoff, S. Unidirectional Digestion with Exonuclease III Creates Targeted Breakpoints for DNA Sequencing, Gene 28:351–359 (1984).

Innis, et al. PCR Protocols, A Guide to Methods and Applications, Academic Press, San Diego, pp. 45–55 (1990).

Matsudaira, P. Sequence from Picomole Quantities of Proteins Electroblotted onto Polyvinylidene Difluoride Membranes, J. Biol. Chem. 282:10, 035–10, 038 (1987).

Allen, Laboratory Techniques in Biochemistry and Molecular Biology, pp. 95–99 and 252–253, Elsevier, Amsterdam, The Netherlands (1989).

Cregg et al., "Recent advances in the expression of foreign genes in *Pichia pastoris*" *Bio/Technology*, 11:905–910 (1993).

Economidou et al., "Quantitative measurements concerning A and B antigen sites" *Vox Sang.*, 12;321–328 (1967).

Fong et al., "Developmental patterns of ABO isoagglutinins in normal children correlated with the effects of age, sex, and maternal isoagglutinins" *Transfusion*, 14:551=559 (1974).

Gilboa et al., "Transfer and expression of cloned genes using retroviral vectors" *BioTechniques*, 4(6);504–512 (1986).

Mollison, "ABO, Lewis Ii and P groups" in *Blood Transfusion in Clinical Medicine*, (Blackwell Scientific Publications, London) pp. 267–327 (1987).

Romano and Mollison, "Red cell destruction in vivo by low concentrations of IgG anti–A" *Br. J. Haematol.*, 29;121–127 (1987).

Schmidt, "The mortality from incompatible transfusion" in *Immunobiology of the Erythrocyte* (Alan R. Liss Inc., NY) pp. 251–261 (1980).

CDNA FOR α-N-ACETYL-GALACTOSAMINIDASE FROM *GALLUS DOMESTICUS*

This application is a Continuation-in-Part of U.S. Ser. No. 08/135,920, filed Oct. 13, 1993, now abandoned.

TECHNICAL FIELD

The present invention relates to a cDNA for α-N-acetyl-galactosaminidase from *Gallus domesticus* and vectors and host cells containing the cDNA.

BACKGROUND OF THE INVENTION

The A, B, and H antigens are a clinically significant blood group (Landsteiner, 1901; Mollison et al., 1987). These antigens are terminal immunodominant monosaccharides on erythrocyte membrane glycoconjugates (Harmening, 1989). High densities of these epitopes are present on erythrocyte membranes and antibodies bound to these antigens readily fix complement (Economidou et al., 1967; Romano and Mollison, 1987). Because these epitopes are ubiquitous in nature, immuno-potent and naturally occurring, complement fixing antibodies occur in individuals lacking these antigens, and transfusion of incompatible blood results in fatal hemolytic transfusion reactions (Fong et al., 1974; Schmidt, 1980).

Complex sugar chains in glycolipids and glycoproteins have often been implicated in the growth and development of eukaryotes (Wantanabe et al., 1976). In particular, complex sugar chains play an important part in the recognition of self in the immune system (Mollison, 1987). Glycosidases (both exoglycosidases and endoglycosidases) are enzymes which can modify carbohydrate membrane epitopes, thereby modulating the immune response (Goldstein et al., 1982). The α-N-acetyl-galactosaminidase from domestic chickens is an enzyme that degrades the human blood group A epitope (Hata et al., 1992). Degradation of the blood group A antigen produces the H antigen, also known as blood group O. Blood group O red blood cells are generally universally transfusable within the ABO blood group system.

The enzyme α-N-acetyl-galactosaminidase [EC 3.2.1.49] is a class of exoglycosidases that have been purified from both procaryotes and eucaryotes (McGuire et al., 1972; McDonald et al., 1972; Kadowaki et al., 1989; Itoh and Uda, 1984; Nakagawa et al., 1987; Kubo, 1989; Weissman et al., 1969; Weissman, 1972). Despite the use of this enzyme because of its ready availability from the livers of domesticated chickens, the use is limited because there are no published reports of preparations that have no detectable protease or other glycosidase activities with proven homogeneity utilizing commercially useful purification methods (Goldstein, 1984). Without a commercially viable method to provide enzymatic activity free of extraneous proteases and glycosidases, there is limited commercial value since the use of a nonhomogeneous enzyme preparation has the potential to damage erythrocyte membranes leading to poor in vivo viability. It would be particularly advantageous to be able to isolate commercially significant amounts of the enzyme from chicken livers because of the low cost of the starting material or to have available cDNA for the enzyme and associated vectors and host cells to enable production of the enzyme in culture.

U.S. Pat. No. 4,330,619, issued May 18, 1982; 4,427,777, issued Jan. 24, 1984; and U.S. Pat. No. 4,609,627, issued Sep. 2, 1986, all to Goldstein, relate to the enzymatic conversion of certain erythrocytes to type O erythrocytes. Since type O erythrocytes can be safely transfused into type A, type B, type A,B recipients, as well as O recipients, type O erythrocytes have significant value in transfusion therapy. The above-mentioned U.S. Pat. No. 4,609,627 discloses the conversion of certain sub-type A and A,B erythrocytes to type O erythrocytes utilizing an α-N-acetyl-galactosaminidase fraction from fresh chicken livers. The patent also discusses the significant potential of such enzymes to be used in the conversion of type $A_2$ erythrocytes to type O erythrocytes.

The Gallus enzyme more specifically has significance because of its specificity for the terminal N-acetyl-α-D-galactosaminyl residues of the human blood group A antigen. Hydrolysis of the terminal N-acetyl-α-D-galactosaminyl monosaccharide results in the less immunogenic type O erythrocyte blood group (Goldstein, 1989). As stated above, the use of a purified Gallus enzyme having significantly increased activity can be an important contributor to enlarging the available compatible blood supply for transfusion therapy.

The purification method for isolating α-N-acetyl-galactosaminidase from chicken livers disclosed in the U.S. Pat. No. 4,609,627 patent requires dehydrating the tissue, extensive protein precipitation steps, extension column chromatography steps, as set forth in FIG. 1, and most importantly, the yields are low compared to the amount of starting material.

Figure 2:
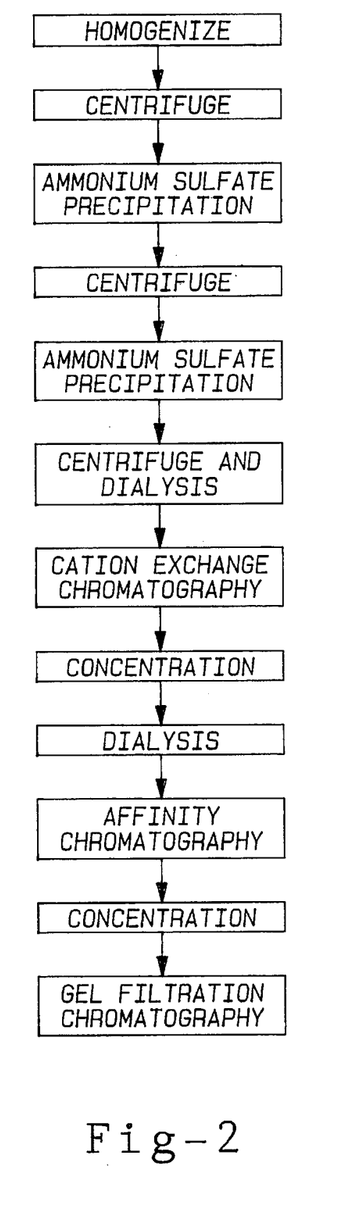
FIG. 2 is a flow chart of the purification scheme as set forth in W.O application US93/10122.

The published application (WO 99409121) of Goldstein and Hurst provides a second purification protocol as set forth in FIG. 2. However, this protocol also requires extensive handling of the tissue, dialysis and more particularly, extensive column chromatography. This type of protocol is expensive, time-consuming, labor intensive and most importantly, the yields are low compared to the amount of starting material. More particularly, the procedure requires the homogenization of 5 pounds (2,270 g) of chicken liver with only 1.8 liter of buffer. This is a 56% w/v homogenate which is a thick, viscous slurry which is inefficiently resolved by filtration or centrifugation. Furthermore, this procedure requires three dialysis steps and two ammonium sulfate precipitations as well as extensive column chromatography.

Modification of isolation procedures to commercial scale cannot always be accomplished by simply increasing the amount of starting material. This does not always increase the yield proportionally. Problems of non-homogeneous product can occur, particularly if steps are eliminated. Further, contamination of the product with proteases and contamination of the column resins often occurs as the amount of material being processed increases.

The present invention provides an improved method of providing isolated and purified glycosidases. The present invention also provides a cDNA for α-N-acetyl-galactosaminidase from *Gallus domesticus* and vectors and host cells containing the cDNA.

SUMMARY OF THE INVENTION AND ADVANTAGES

The present invention is a cDNA for α-N-acetyl-galactosaminidase from *Gallus domesticus* and vectors and host cells containing the cDNA.

BRIEF DESCRIPTION OF THE FIGURES

Other advantages of the present invention will be readily appreciated as the same becomes better understood by reference to the following detailed description when considered in connection with the accompanying drawings wherein:

FIG. 5-A shows a SDS-PAGE separation wherein lanes 2 and 4 are molecular weight standards of 97.4, 66.2, 45.0, 31.0, 21.5, and 14.4 kDa and lanes 1 and 3 are unreduced (M.W.=44.2 kDa) and reduced (M.W.=49.1 kDa) α-N-acetylgalactosaminidase;

FIG. 5-B is a graph showing the results of a gel filtration separation wherein molecular weight standards are indicated by □ and α-N-acetylgalactosaminidase is indicated by O (M.W.=145.0 kDa);

FIG. 6-A is a graph showing a gel filtration separation wherein activity is shown by □, units/ml, as a function of fraction number;

FIG. 6-B shows the results of an SDS-PAGE separation wherein lane 1 and 10 are molecular weight standards of 97.4, 66.2, 45.0, 31.0, 21.5, and 14.4 kDa and lanes 2-9 are fractions 45-52 as shown in FIG. 6-A of unreduced α-N-acetylgalactosaminidase (M.W. approximately 44.2 kDa);

FIG. 7-A is a graph showing enzyme activity as a function of pH;

FIG. 7-B is a graph showing enzyme activity as a function of ionic strength wherein data points in FIGS. 7-A and 7-B are the means of three independent determinations;

FIG. 9 is amino acid comparison of the deduced chicken α-N-acetylgalactosaminidase {αNAG (c)} protein with the human α-N-acetylgalactosaminidase {αNAG (h)}, human α-galactosidase A {αGALA (h)}, yeast α-galactosidase {αGAL (y)} and a plant α-galactosidase {αGAL (p)}, amino acids that are conserved are shown white on black, dashes represent gaps introduced to obtain the optimal alignment.

DETAILED DESCRIPTION OF THE INVENTION

The present invention provides the composite cDNA sequence of 2315 nucleotides and its predicted protein sequence for α-N-acetylgalactosaminidase are shown in SEQ ID Nos:1 and 2. It contains an uninterrupted open reading frame of 1215 nucleotides that would encode a polypeptide of 405 amino acids with a predicted molecular mass of 45,605 daltons. This is in good agreement with the estimated size of the α-N-acetylgalactosaminidase isolated from chicken liver which has a relative molecular weight of 44,500 (Hata et al., 1992).

The deduced amino acid sequence of the chicken α-N-acetyl-galactosaminidase is highly conserved with the human α-N-acetylgalactosaminidase and the α-galactosidases of several species. The chicken enzyme has 75% identity with the human α-N-acetylgalactosaminidase enzyme (Tsuji et al., 1989), 56% identify with human e-galactosidase A (Koide et al., 1990), 33% identify with yeast α-galactosidases (Sumner-Smith et al., 1985) and 38% identity with an α-galactosidase obtained from the guar plant (Overbeeke et al., 1989).

Most of the similarity resides in the first 300 amino acids of these enzymes, with a substantial amount of variation in the carboxy terminal 100 amino acids. There are 48 amino acids that are conserved between all six enzymes, including 5 invariant cysteines (FIG. 9). These conserved residues may play an important role in catalysis or in maintaining the correct structure of this family of related enzymes.

Vectors can be constructed containing the cDNA of the present invention by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. The host cell can be any eucaryotic and procaryotic cells, which can be transformed with the vector and which will support the production of the enzyme. *E. coli* and *Pichia pastoris* are host cells in bacterial and yeast (Cregg et al, 1993) preferred embodiments, respectively. Methods for transformation can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995) and Gilboa, et al. (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or ex vivo. Viral vectors can also be modified with specific receptors or ligands to alter target specificity through receptor mediated events.

The present invention also provides a method of purifying and isolating an glycosidase from tissue. The method includes the steps of preparing a protein tissue or body fluid extract containing the enzyme. The enzyme is then isolated from the tissue extract by first performing a cation exchange batch separation, then second performing an anion exchange batch separation, and then passing through an affinity column. The active fractions containing the enzyme having passed through the columns are then collected, pooled and concentrated.

In particular, in the present invention the batch separation steps required only mixing, they are not chromatography steps with the resulting ease of performance and ability to process more material. The tissue from which the enzyme is extracted is selected by screening for a tissue high in content of the glycosidase coupled with ease in obtaining the tissue. As used herein, the term tissue can encompass body fluids as well.

The present invention also matches the affinity ligand to the glycosidase or glycosidase that is being isolated. For example, α-N-acetylgalactosaminidase from *Gallus domesticus* is matched with an ξ-aminohexanoyl-α-D-galactopyranosylamine Affi-Gel™ 10 column.

Figure 1:
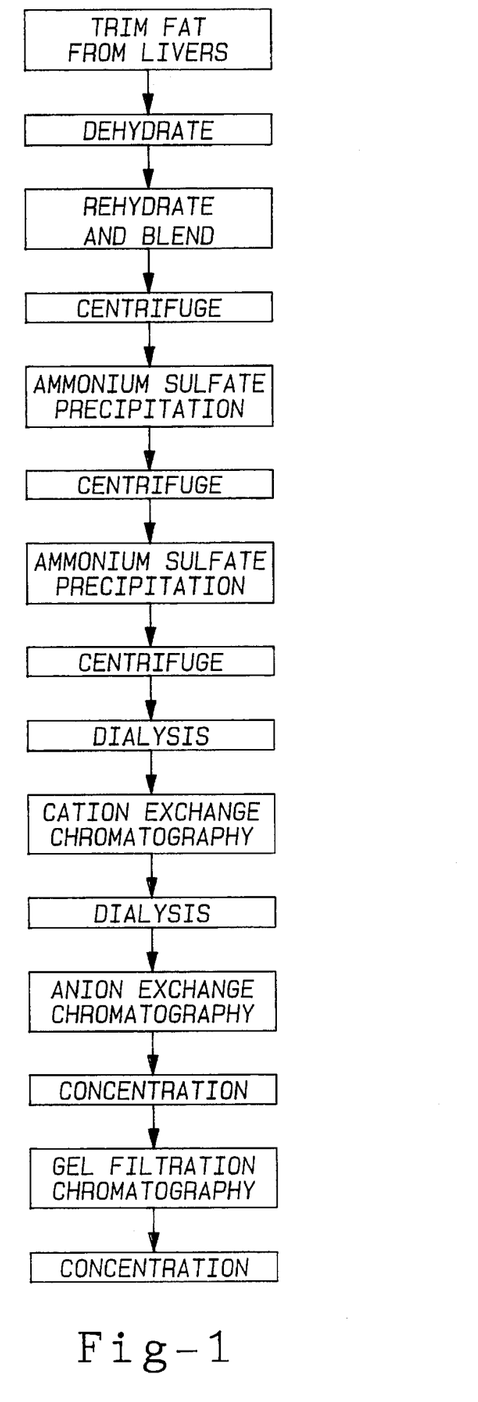
FIG. 1 is a flow chart of the purification scheme of the prior art U.S. Pat. No. 4,609,627.
Figure 3:
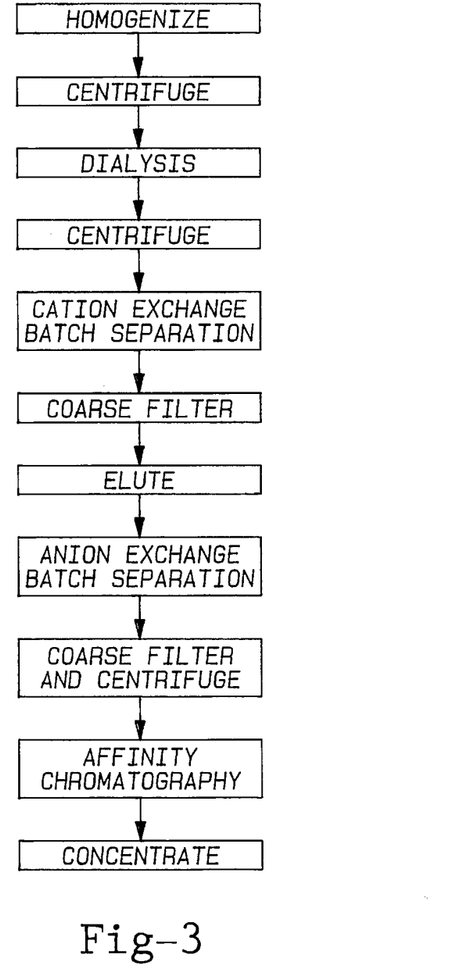
FIG. 3 is a flow chart of the preferred embodiment of the present invention.
Figure 4:
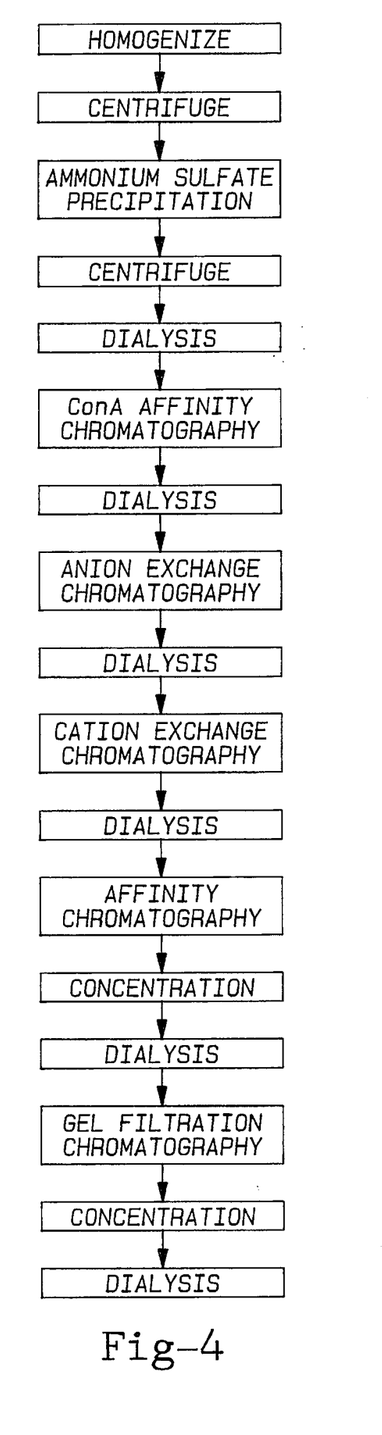
FIG. 4 is a flow chart of a second embodiment of the present invention.

As an exemplar, a method of purifying and isolating α-N-acetyl-galactosaminidase from *Gallus domesticus* as shown in FIG. 3 and described in Example 2 is disclosed. The method includes the steps of preparing a tissue extract containing tissue proteins including the enzyme. The preparation includes mincing and homogenizing at 4° C. either fresh or frozen avian liver and collecting a supernatant containing the enzyme as described in Example 2. This step contrasts with the prior art which required trimming the fat from the livers, dehydrating and rehydrating (FIG. 1) as well as ammonium sulfate precipitations (FIGS. 1, 2 and 4).

In the method of the present invention, the supernatant from the previous step which contains the tissue extract is centrifuged, dialyzed and then recentrifuged as described in Example 2. The extract is mixed with a cation exchange resin for batch separation. The mixture that is formed is stirred for three hours. To isolate the tissue extract including the enzyme, the resin from the batch separation is removed by filtration from the mixture and the extract eluted from the resin. After this separation step, the specific activity has increased from 0,017 to 0.069 U mg$^{-1}$min$^{-1}$. Approximately 88% of the contaminating proteins have been removed at this step.

The cation exchange resin is selected from carboxymethyl (CM) cellulose, CM52, CM agarose, CM sepharose and sulfopropyl (SP) Sephadex with SP Sephadex C-50 the preferred cation resin. Other cation exchange resins as are known to those skilled in the art may also be suitable.

The eluate from the cation batch separation is mixed with an anion exchange resin forming a second mixture and stirred for anion exchange batch separation. The anion exchange resin is selected from diethylaminoethyl (DEAE) cellulose, DEAE sephacel, DEAE sepharose, QAE (Diethyl-[2-hydroxylpropyl]aminoethyl) cellulose and QAE sephadex, with DEAE Sephadex A-50 being the preferred anion resin. Other anion exchange resins as are known to those skilled in the art may also be suitable.

The batch separations eliminate the column chromatography steps in the prior art methods. In the prior art methods shown in FIGS. 1 and 2, cation exchange column chromatography followed by dialysis and then anion exchange column chromatography is utilized. In the prior art method shown in FIG. 2, cation exchange column chromatography, as well as gel filtration column chromatography, is used. The present invention eliminates the need for these column chromatography steps for the simpler batch method of mixing the resin with the supernatant, stirring for a short period of time and separation by filtration through a coarse fritted funnel.

The second mixture is then filtered and the filtrate is reserved, centrifuged, and then loaded on an affinity column with the appropriate ligand such as ξ-aminohexanoyl-α-D-galactopyranosylamine. The affinity resin in a preferred embodiment is Affi-Gel™ 10, but others known to those skilled in the art may be used. Active fractions are collected from the column, pooled and concentrated utilizing, in a preferred embodiment, an Amicon Ultrafiltration cell. The yield from this method was 6–7 mg of purified enzyme per 900 grams of starting livers.

Of significance with regard to the increased activity of the purified enzyme preparation is the use in accordance with the present invention of ξ-aminohexanoyl-α-D-galactopyranosylamine affinity resin during the isolation procedure. By using this resin, the present invention provides a preparation having greatly reduced contamination by β-N-acetylhexosaminidases. Prior preparations from mammalian liver had a problem with regard to this contamination, thereby not being able to achieve homogeneity.

This method significantly reduces the number of columns required in the prior art. Further, it reduces the need for detergent stabilization of the isolated enzyme. Detergent was originally used, as shown in Example 1, to enhance recovery from dilute protein concentrations. In the present invention, the preparations are only dilute after affinity chromatography and for less than 24 hours. The preparations are immediately concentrated and thus stabilized. Therefore, the detergent is no longer needed.

A second method of purifying and isolating an enzyme α-N-acetyl-galactosaminidase from *Gallus domesticus* as shown in FIG. 4 and described in Example 1 is disclosed. The method includes preparing a tissue extract which includes the steps of homogenizing the livers, followed by centrifugation, ammonium sulfate precipitation, centrifugation and dialysis. The dialysate is centrifuged and applied to a ConA affinity column. Care must be taken to monitor the ConA column for contamination with precipitated and nonspecifically bound protein from the crude preparations.

The active fractions from the column are pooled, dialyzed and subjected to anion exchange column chromatography followed by dialysis and cation exchange column chromatography. The active fractions were again pooled, dialyzed and applied to an ξ-aminohexanoyl-α-D-galactopyranosylamine Affi-Gel™ 10 column. Active fractions are collected from the column, pooled, concentrated, dialyzed and passed over a gel filtration column. The active fractions were concentrated and dialyzed. The yield from this method was 0.4 mg of purified enzyme per 500 grams of starting tissue.

A purified α-N-acetyl-galactosaminidase preparation is prepared from these methods, the preparation being derived from Gallus domesticus, the domestic chicken. As discussed herein, the enzyme is an exoglycosidase which degrades the human blood group $A_2$ epitope. The present invention is the result of a development of a technique to purify the enzyme to homogeneity rapidly and in high yield.

As derived from the present invention, the enzyme as purified is characterized as follows. The enzyme has a molecular weight of 46.7 kDa by SDS-PAGE and 123.7 kDa by gel filtration. The enzyme is homogeneous and has no measurable protease activity. Significantly, the enzyme has a pH optimum of 3.3 to 3.4 and a pI of approximately 7.5 to 8.5 by chromatofocusing. The enzyme is unaffected by increasing ionic strength and stable at 4° C. The enzyme preparation is highly selective for PNP-N-acetyl-α-D-galactosaminide. More specifically, the specific activities range from 63.95 to 77.42 units per milligram per minute with 1.0 mM ONP-N-acetyl-α-D-galactosaminide and 68.31 to 73.33 units per milligram with 2.5 mM PNP-N-acetyl-α-D-galactosaminide as substrate.

The homogeneity of the enzyme preparation for the N-acetyl-α-D-galactosaminyl residue is critical since various galactosyl and glucosaminyl residues are abundant terminal saccharide residues on erythrocyte membranes. Additionally, numerous other blood group antigens bear immunodominant monosaccharides (Issitt, 1985). Additionally, glycoproteins bearing the MNSs blood group antigens are rich in neuraminic acid (Dahr, 1986). Non-specific removal of neuraminic acid residues from erythrocyte membranes results in the T phenotype with associated polyagglutination (Uhlenbruck et al., 1969). Furthermore, removal of neuraminic acid from red blood cells markedly shortens their survival in vivo. Accordingly, the absence of neuraminidase activity is important if glycosidase preparations are used to modify blood group antigens. This is because other glycosidase activities can potentially produce neoantigens. The preparations of the present inventive isolation methods lack other detectable glycosidase activities and, therefore, are quite valuable with regard to this critical issue.

Another critical issue is whether the preparations have proteolytic activity. Numerous erythrocyte antigens such as the Duffy and MNSs blood groups can be degraded by exogenous proteases (Harmening, 1989). Again, proteolytic modification can create neoantigenicity or rapid clearance from the circulation. The preparations isolated by means of the present invention lacked detectable aminopeptidase and endoprotease activities.

The above discussion provides a factual basis for the use of novel isolation procedure for glycosidases as shown for the exemplar α-N-acetylgalactosaminidase isolated from chicken liver. The methods used with and the utility of the present invention can be shown by the following examples.

The following section demonstrates the isolation protocols, characterization of the purity of the enzyme preparation from this protocol, its cDNA sequence, and its utility for deantigenation.

EXAMPLES

GENERAL METHODS:

Chemicals: Affi-Gel™ 10 and SDS polyacrylamide gels were purchased from Bio-Rad, Richmond, Calif. CM Sephadex C-50 and DEAE Sephadex A-S0 were obtained from Sigma (St. Louis, Mo.). Endoprotease substrates were obtained from Boehringer Manneheim (Indianapolis, Ind.). All other chemicals, substrates, and chromatography resins were the highest purity available from Sigma Chemical Company, St. Louis, Mo., or Aldrich, Milwaukee, Wis. Antisera was purchased from Immucor, Norcross, Ga. and Ortho Diagnostic Systems, Raritan, N.J. Fresh chicken livers were obtained from a local commercial supplier.

Synthesis of affinity ligand and resin: ξ-aminohexanoyl-α-D-galactopyranosYlamine was synthesized by a modification of the method of Harpaz et al. (1974). Purity of the product was determined by thin-layer chromatography and mass spectroscopy. The ligand was coupled to Affi-Gel™ 10 per the manufacturer's directions. Coupling efficiencies of 80%.

Analytical procedures: Protein concentration was quantitated by the BCA method (Smith et al., 1985). Enzymatic activity was quantitated during the purification by measuring production of p-nitrophenol (PNP) from PNP-N-acetyl-α-D-galactosaminide or o-nitrophenol (ONP) from ONP-N-acetyl-α-D-galactosaminide. Enzyme aliquots were incubated in 200 μl of 50 mM Na citrate+1 mg/ml BSA+1.0 mM PNP-N-acetyl-α-D-galactosaminide, pH 3.5, at 37° C. The reactions were quenched with 1.0 ml of 0.25M $Na_2CO_3$ and the OD 405 nm was measured. One unit of activity was defined as 1.0 μmole of substrate hydrolyzed per minute.

Substrate specificity studies were performed in the same buffer with p-nitrophenyl (PNP) conjugates at a 2.5 mM concentration and pH 3.5. Activity against the 4-methylumbelliferyl (4-MU) substrates was performed by an adaptation of the method of Dean et al. (1977a).

The pH optima was determined by incubating aliquots of the enzyme in 40 mM Na citrate+40 mM $NaH_2PO_4$+1 mg/ml BSA+2.5 mM PNP-N-acetyl-α-D-galactosamide, pH 2.0 to 8.0. The ionic strength optimum was determined by incubating aliquots of the enzyme in 2.5 mM Na citrate+1 mg/ml BSA+2.5 mM PNP-N-acetyl-α-D-galactoside+0 to 1.0M NaCl, pH 3.5 and 6.0. The Kms for ONP- and PNP-N-acetyl-α-D-galactosaminide were determined by varying the substrate concentration in 50 mM Na citrate+1 mg/ml BSA, pH 3.5. The native molecular weight was determined by applying a concentrated portion of the enzyme to a 1×45 cm Sephacryl S-200 column equilibrated in 25 mM Na citrate+200 mM NaCl, pH 6.0. SDS polyacrylamide electrophoresis (SDS-PAGE) was performed according to the method of Laemmli and the protein bands developed with Coomassie R-250 (Laemmli, 1970). Amino acid composition was determined on a Beckman amino acid analyzer (Moore et al., 1954).

Aminopeptidase assays were performed by incubating aliquots of enzyme with 2.5 mM of various p-nitroaniline (PNA) substrates in 50 mM Na citrate+50 mM $NaH_2PO_4$+ 0.1% Triton X-100, pH 5.0 to 8.0 (Macfarlane et al., 1988). The reactions were incubated at 37° C., quenched with 1.0 ml of 0.25M $Na_2CO_3$, and the OD 405 nm was determined. One unit of aminopeptidase activity was defined as 1.0 μmole of PNA hydrolyzed per minute.

Endoprotease assays were performed by an adaption of the resorufin-labeled casein assay of Twining (Twining, 1984). The limit of sensitivity of this assay was determined using a trypsin standard. Stable, concentrated, detergent-free enzyme was prepared as described herein. Activity against the blood group antigen on erythrocytes was determined by incubating enzyme at 24°–37° C. for 2–8 hours with either erythrocytes equilibrated in 25 mM Na citrate+50 mM $NaH_2PO_4$+80 mM NaCl, pH 5.6–5.8, or in 2.5–5 mM Na citrate+300 mM glycine, pH 5.4–5.6. The cells were washed with phosphate buffered saline, pH 7.0, then incubated with varying dilutions of polyclonal or monoclonal antibody, as for example anti-A for A erythrocytes. Other antibodies and buffers could be used for other blood groups as is known in the art. Hemagglutination was performed and titer scored by standard methods (Bryant, 1982).

EXAMPLE 1

Purification of the enzyme as set forth in FIG. 4: As a first method of improving yield and ease of isolation, the protocol, as set forth in FIG. 4 and described hereinbelow, was developed. This method improved the yield and homozygosity of the enzyme preparation over the prior art. The yield, in general, from this method is 0.4 mg of extremely pure enzyme from 500 grams of chicken liver as compared to the prior art yields of 300 mg of enzyme from 200 pounds of chicken liver (FIG. 2 scheme).

Each of the following steps were carried out at 4° C. to minimize proteolysis:

Step 1. 500 g of fresh liver was drained, washed with 150 mM NaCl, drained again, and homogenized in a Waring blender with 1 L of 25 mM Tris HCl+5 mM $CaCl_2$+0.01% $NAN_3$, pH 7.5. The volume of the resultant homogenate was adjusted to 1.5 L, as necessary, with 25 mM Tris HCl+5 mM $CaCl_2$+0.01% $NAN_3$, pH 7.5, allowed to incubate with occasional stirring for 30 minutes, and centrifuged at 6,844×g for 30 minutes. To the supernatant, ammonium sulfate was slowly added to 50% saturation and allowed to incubate for one hour. The precipitate was harvested by centrifugation at 6,844×g for one hour, reserved, suspended in 1 L of 25 mM Tris HCl+5 mM $CaCl_2$+0.01% $NaN_3$, pH 7.5, and dialyzed exhaustively into the same buffer. The dialysate was then centrifuged at 6,844×g for 2.5 hours.

Step 2. $MgCl_2$ and $MnCl_2$ were added to the dialysate to final concentrations of 1 mM. The preparation was loaded onto a 5×15 cm column of Con A Sepharose-4B equilibrated in 25 mM Tris HCl+5 mM $CaCl_2$+1 mM $MgCl_2$+1 mM $MnCl_2$+0.01% $NaN_3$, pH 7.5. The column was washed with 400 mls of the same buffer and then developed with 600 mls of 25 mM Tris HCl+100 mM methyl-α-D-mannopyranoside+5 mM $CaCl_2$+1 mM $MgCl_2$+1 mM $MnCl_2$+0.1% Triton X-100+0.01% $NaN_3$, pH 7.5. Detergent was added to enhance recovery and stabilize the enzyme. The active fractions from the broad eluting peak were pooled and dialyzed exhaustively into 10 mM Tris HCl+0.1% Triton X-100+0.01% $NaN_3$, pH 7.5.

Step 3. The dialysate was then loaded onto a 2.5×20 cm DEAE-Sephadex A-50 column equilibrated in 10 mM Tris HCl+0.1% Triton X-100+0.01% $NaN_3$, pH 7.5. The flow through was collected and dialyzed exhaustively into 10 mM Na acetate+0.1% Triton X-100+0.01% $NaN_3$, pH 5.0.

Step 4. The dialyzed preparation was loaded onto a 1.5×20 cm SP-Sephadex C-50 column equilibrated in 10 mM Na acetate+0.1% Triton X-100+0.01% $NaN_3$, pH 5.0. The column was washed with 70 mls of equilibration buffer, and the enzyme was eluted with a 500 ml linear gradient of 10 mM Na acetate+0 to 500 mM NaCl+0.1% Triton X-100+ 0.01% $NaN_3$, pH 5.0. The active fractions were pooled and exhaustively dialyzed into 50 mM Na acetate+0.1% Triton X-100+0.01% $NaN_3$, pH 5.0.

Step 5. After dialysis, the pool was applied to a 1.5×20 cm ξ-aminohexanoyl-α-D-galactopyranosylamine Affi-Gel™ 10 column equilibrated in 50 mM Na acetate+0.1% Triton X-100+0.01% $NaN_3$, pH 5.0. The column was washed with 90 mls of equilibration buffer, and the enzyme was eluted with 50 mM $NaH_2PO_4$+100 mM methyl-α-D-galactopyranoside+0.1% Triton X-100+0.01% $NaN_3$, pH 7.0. Active fractions were pooled, concentrated, and dialyzed into 50 mM Na acetate+0.1% Triton X-100+0.01% $NaN_3$, pH 5.0.

Step 6. The dialyzed preparation was loaded onto a 1.5×60 cm Sephacryl S-200 column equilibrated with 50 mM Na acetate+0.1% Triton X-100+0.01% $NaN_3$, pH 5.0. The column was developed with the same buffer. Active fractions were pooled, concentrated, dialyzed into 50 mM Na acetate+0.1% Triton X-100+0.01% $NaN_3$, pH 5.0, and stored at 4° C.

Analysis of Purified Enzyme: As shown in Table I, purification of the enzyme was achieved with acceptable recoveries. Affinity chromatography on Con A Sepharose and ξ-aminohexanoyl-α-D-galactopyranosylamine Affi-Gel™ 10 removed the bulk of contaminating protein. The specific activities of the purified enzyme ranged from 30.37 to 74.26 units per milligram per minute (mean=47.42, S.D.= 17.34, N=5) with 1.0 mM ONP-N-acetyl-α-D-galactosaminide, or from 40.69 to 99.50 units per milligram (mean=63.55, S.D.=23.33, N=5) with 2.5 mM PNP-N-acetyl-α-D-galactosaminide as the substrate. There was a 1,684 fold purification with an average recovery of 3.55%. The enzyme was stable at 4° C. for several months with less than 10% loss of activity.

Figure 5A:
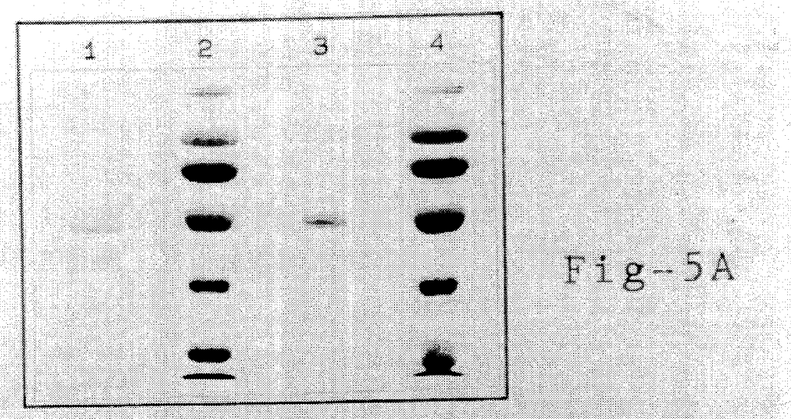
Figure 5B:
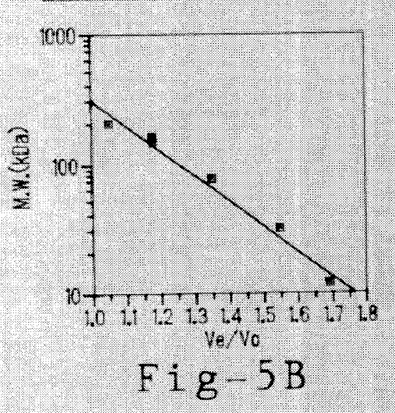

The purified preparations had a single detectable band on a 12% Coomassie stained SDS gel. The mean molecular weight determined by SDS-PAGE under reducing conditions was 49.1 kDa (S.D.=3.0, N=6) and 44.2 kDa (S.D.=1.9, N=6) under nonreducing conditions as shown in FIG. 5-A. The mean native molecular weight was 145.0 kDa (S.D.= 12.5, N=3) as determined by gel filtration on Sephacryl S-200, FIG. 5-B.

Figure 6A:
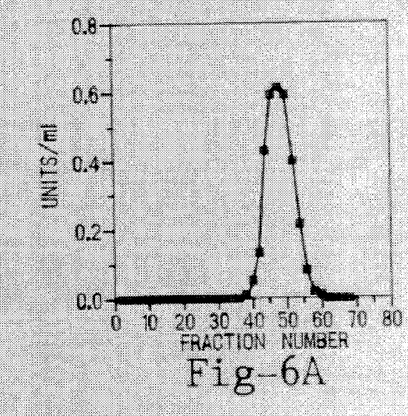
Figure 6B:
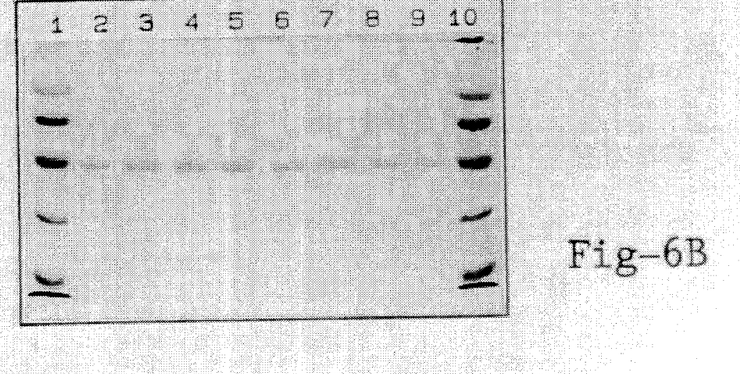

SDS-PAGE and enzymatic activity measurements were performed on the S-200 column fractions, and the amount of enzymatic activity in the peak fractions correlated with the staining intensity of the 49.1 kDa band on the SDS gels, FIG. 6. Amino acid composition data is presented in Table II. The molecular weight calculated from compositional data was 50.0 kDa. The enzyme chromatofocused as a single peak of activity with an approximate mean pI of 8.15.

Figure 7A:
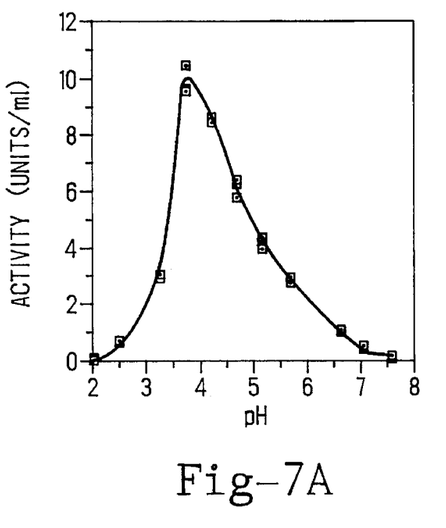
Figure 7B:
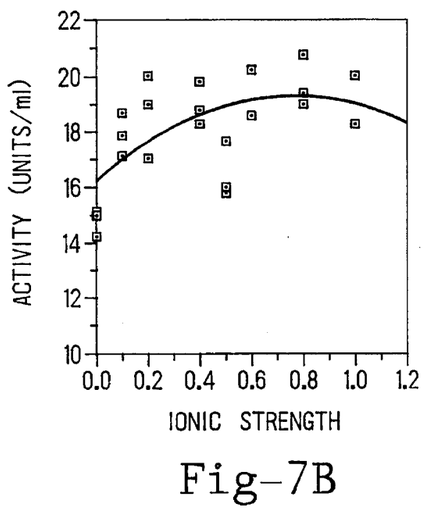

In activity tests on a variety of substrates, specificity was shown using N-acetyl-α-D-galactosaminide and galactopyranoside conjugates. The Km and turnover numbers for ONP-N-acetyl-α-D-galactosaminide, PNP-N-acetyl-α-D-galactosaminide, and PNP-α-D-galactopyranoside are summarized in Table III. Sugars, other than N-acetyl-α-D-galactosaminide or α-D-galactose, showed no activity, Table IV. The enzyme had a broad pH range with the optima at 3.7, FIG. 7-A. The enzyme was not strongly inhibited by high or low ionic strengths at pH 3.7, FIG. 7-B.

The subunit molecular weight of the isolated Gallus α-N-acetyl-galactosaminidase was similar to that reported for other eucaryotes. For example, the porcine and human enzymes had 52 and 48 kDa subunits, respectively (Sung et al., 1980; Dean et al., 1979). The reported values for the native porcine and human enzymes were 102 and 117 kDa, respectively (Sung and Sweeley, 1980; Dean et al., 1979). The observed molecular weight of 145 kDa implies that native Gallus enzyme probably exists as a dimer, trimer or possibly a tetramer of the 49.1 kDa subunit. α-N-acetyl-galactosaminidase from the limpet, *Patella vulgata*, is a tetramer of 45 kDa subunit (Uda et al., 1977).

Hydrolysis of α-D-galactosyl conjugates by α-N-acetyl-galactosaminidase has been observed by other investigators (Dean et al., 1977a). For the human enzyme, the reported Km for PNP-α-D-galactopyranoside, 1 mM (Schram et al, 1977). Gallus α-N-acetyl-galactosaminidase also had a high Km for PNP-α-D-galactopyranoside. The galactopyranoside analog ξ-aminohexanoyl-α-D-galactopyranosylamine was shown to be an efficient active site specific affinity ligand for the Gallus enzyme. This same affinity ligand was used to purify human placental α-N-acetyl-galactosaminidase (Kusiak et al., 1978).

No proteolytic activity was detected in the purified preparations. Aminopeptidase activity was below the limits of detection, ≦0.05 units/mg enzyme, with the following substrates: PNA-alanine, PNA-lysine, PNA-leucine, PNA-proline, and PNA-alanine-valine. In a resorufin-labeled casein assay with a sensitivity limit of 0.01 trypsin BAEE units, ≦0.01 BAEE units/mg enzyme was detected. This corresponds to less than 0.78 ng of "trypsin-like activity" per mg of pure enzyme.

EXAMPLE 2

Purification of the enzyme as set forth in FIG. 3: A batch method for isolation the protocol as set forth in FIG. 3, and described hereinbelow, was developed. This method improved the yield and homozygosity of the enzyme preparation over the prior art. The yield, in general, from this method is 6–7 mg per 900 g of chicken liver.

1. Mince 900 g of fresh or frozen chicken liver. Add minced liver to 200 g of acid washed glass beads and 1.5 L of 10 mM $NaH_2PO_4$, pH 5.5. The pH range can be 3.0 to 8.0 using a buffer species with an appropriate pKa. Homogenize in a water cooled Waring blender with four 15 sec low speed bursts and four 15 sec high speed bursts at 4° C. Allow the glass beads to settle from the solution for 10 min at 4° C. and decant the supernatant.

2. Centrifuge the supernatant at 6844×g at 4° C. for one hour. Harvest the supernatant by filtering through glass wool. Repeat centrifugation for two hours and harvest.

3. Dialyze the supernatant against 3×10 L changes of 10 mM NaH$_2$PO4, pH 5.5 (range 4 to 6, with a buffer species with an appropriate pKa) at 4°.

4. Centrifuge the dialysate at 6844×g at 4° C. for two hours and harvest.

5. Add 300 ml (range 25 to 900) of SP Sephadex C-50 cation exchange ion exchange resin equilibrated in 10 mM Na H$_2$PO$_4$, pH 5.5 (range 4 to 6, with a buffer species with an appropriate pKa) to the dialysate, pH 5.5. Stir at low speed for one to 24 hours at 4° C. Separate the supernatant from the resin by filtration through a coarse fritted funnel. Wash the resin with an additional volume of 300 ml (range 50 to 2000) of 10 mM NaH$_2$PO$_4$. Discard the filtrate. Elute the enzyme by adding 500 ml of 10 mM NaH$_2$PO$_4$+200 mM NaCl, pH 5.5 at 4° C. Let it filter slowly by gravitational force, stirring occasionally. Reserve the eluate.

6. Mix the eluate with 100 ml (range 10 to 300 ml) DEAE Sephadex A-50 anion exchange resin (equilibrated with 10 mM NaH$_2$PO$_4$, pH 5.5). Stir at low speed for one to 24 hours at 4° C. Separate the supernatant from the resin by filtration through a coarse fritted funnel. Wash the resin with an additional volume of 200 ml of 10 mM NaH$_2$PO$_4$, pH 5.5. The filtrate is reserved.

7. Load the filtrate onto a 2.5×15.0 cm ε-amino-hexanoyl-α-D-galactopyranosylamine Affi-Gel™ 10 column equilibrated with 10 mM NaH$_2$PO$_4$, pH 5.5 at 4° C. Wash the column with 300 ml of 75 mM NaH$_2$PO$_4$ pH 5.5. Elute the enzyme from the column with 300 ml (range 50 to 500) of 50 mM NaH$_2$PO$_4$+100 mM D-(+)-Galactose, pH 7.0.

8. Concentrate using an Amicon Ultrafiltration cell (YM 10 membrane with 5 mM Na Citrate, pH 5.6).

The pH of buffers can be varied if the buffer species used has the appropriate pKa to what is listed herein. The final product can be filter sterilized and/or placed in other buffers for further use.

Analysis of Purified Enzyme: As shown in Table V, rapid, batch purification of the enzyme was achieved with recoveries better than in the prior art. The specific activities of the purified enzyme ranged from 63.95 to 77.42 units per milligram per minute (mean=72.92, S.D.=7.77, N=3) with 1.0 mM ONP-N-acetyl-α-D-galactosaminide, or from 68.31 to 73.33 units per milligram (mean=71.03, S.D.=2.54, N=3) with 2.5 mM PNP-N-acetyl-α-D-galactosaminide as the substrate. There was a 3,946 fold purification with an average recovery of 57.6%.

The enzyme was stable at 4° C. for six months with less than 5% loss of activity. The purified preparations had a single band on a 12% Coomassie stained SDS gel.

The mean molecular weight determined by SDS-PAGE under reducing conditions was 48.65 kDa (S.D.=2.51, N=6) and 46.71 kDa (S.D.=1.75, N=6) under nonreducing conditions. The mean native molecular weight was 123.67 kDa (S.D.=7.51, N=3) as determined by gel filtration on Sephacryl S-200.

SDS-PAGE and enzymatic activity measurements were performed on the S-200 column fractions, and the amount of enzymatic activity in the peak fractions correlated with the kDa band. The enzyme chromatofocused as a single peak of activity with an approximate mean pI of 7.5 to 8.5.

In activity tests on a variety of substrates, specificity was shown using N-acetyl-α-D-galactosaminide and galactopyranoside conjugates. The Km and turnover number for PNP-N-acetyl-α-D-galactosaminide are 0.86 mM (mean= 0.86, S.D.=0.03, N=3) and 3318.0 moles substrate/mole enzyme/minute (mean=3318, S.D.=118.5, N=3). Sugars, other than N-acetyl-α-D-galactosaminide or α-D-galactose, showed no detectable activity, Table VI.

The enzyme had a broad pH range with the optima at 3.4. The enzyme was not significantly affected by high ionic strengths at pH 3.5. No proteolytic activity was detected in the purified preparations. Aminopeptidase activity was less than 0.05 units per mg, with the following substrates: PNA-alanine, PNA-lysine, PNA-leucine, PNA-proline, and PNA-alanine-valine. In a resorufin-labeled casein assay with a sensitivity limit of 0.01 trypsin BAEE units, less than 0.01 BAEE units/mg enzyme was detected. This corresponds to less than 0.78 ng of "trypsin-like activity" per mg of pure enzyme.

EXAMPLE 3

To obtain a cDNA clone encoding the mature chicken α-N-acetylgalactosaminidase enzyme applicants screened a chicken liver λZAP cDNA library (Stratagene) with a synthetic oligonucleotide derived from the DNA sequence of the human α-N-acetyl-galactosaminidase gene (Tsuji et al., 1989; Wang et al., 1990). The double stranded oligonucleotide probe was synthesized by dual asymmetric PCR (Sandu et al., 1992) using four overlapping oligonucleotides:

GCGGATCCGATGCTCAGACCTTCGC-
CGAGTGGAAGGTAGACATGCTCAAGC
TGGATGGC (SEQ ID No:3);

ATTCAGGGCAGCAGCCATCTTGGGGTAC-
CCCTGGGCCCGCTCCTCGGGGGT GGAGAAG-
CAGCCATCCAGCTTGAG (SEQ ID No:4);

GCTGCTGCCCTGAATGCCACAGGCCGC-
CCCATCGCCTTCTCCTGC (SEQ ID No:5); and

GCGAATTCGCAGGAGAAGGCGAT (SEQ ID No:6).

The PCR product was isolated by gel electrophoresis, (Sambrook et al., 1989) labeled (Feinberg et al., 1983) and used to screen approximately 200,000 plaques under low-stringency of hybridization conditions as previously described (Walker, 1993). One hybridizing plaque was isolated and purified by standard techniques (Sambrook, 1989). The cDNA clone was excised as described by the supplier (Stratagene) and used to construct nested deletions (Henikoff, 1984) that were sequenced with Sequenase (U.S. Biochemical). This initial clone represented nucleotides 162–2315 of the chicken α-N-acetylgalactosaminidase cDNA sequence (SEQ ID No.1). The 5' end of the cDNA clone was obtained by RNA-PCR (Innis et al., 1990) using oligonucleotide primers corresponding to nucleotides 1–22 and 234–257, with the sequence of the 5' primer being derived from the genomic DNA sequence of the chicken α-N-acetylgalactosaminidase gene.

To confirm that the cDNA clone encodes the chicken α-N-acetyl-galactosaminidase enzyme, the deduced amino acid sequence was compared to amino terminal and two cyanogen bromide derived peptide sequences obtained from the enzyme purified from chicken liver. Amino terminal sequence data was obtained by Western blotting onto PVDF membrane with subsequent sequencing (Matsudaira, 1987). Internal sequence data was obtained by cyanogen bromide digestion, peptide purification by HPLC and solid phase sequencing using conventional methods (Allen, 1989). The protein sequence data is identical to the deduced amino acid sequence as shown in SEQ ID No:2. This confirms that the cDNA clone corresponds to the region of the mRNA encoding the mature polypeptide for the chicken α-N-acetylgalactosaminidase.

EXAMPLE 4

Figure 8:
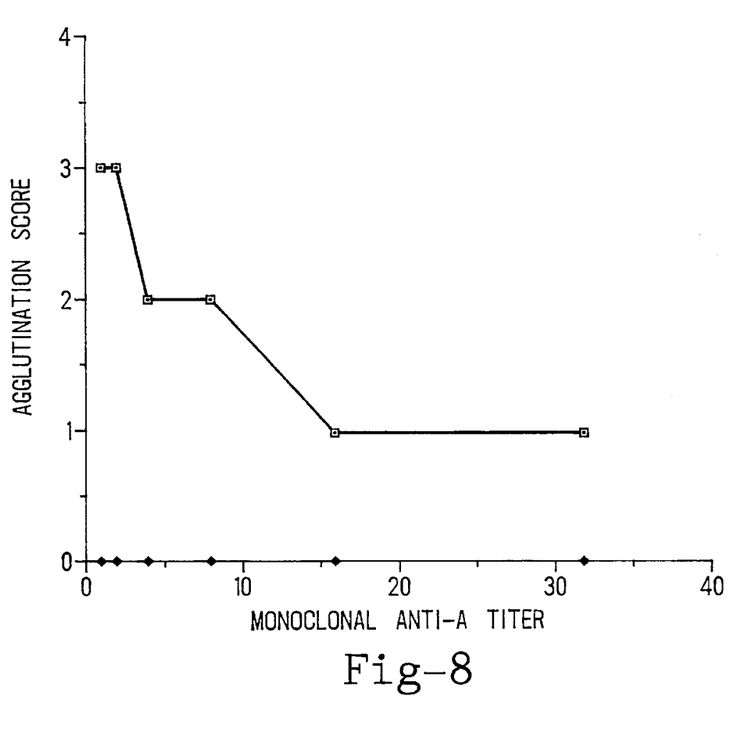
FIG. 8 is a graph showing enzyme activity against the blood group $A_2$ erythrocyte terminal N-acetyl-α-D-galactosaminyl residues wherein □=−α-N-acetyl-galactosaminidase and ♦=+α-N-acetyl-galactosaminidase wherein 0 indicates no agglutination and 4 indicates complete agglutination, data points being the mean of duplicate determinations.

The enzyme was also tested on human $A_2$ erythrocytes. Removal of the terminal N-acetyl-α-D-galactosaminyl residue from the blood group A epitope, {galNAc(α1–3) gal(β1-R) {fuc(α1–2)} glueNAc(β1-R)}, was achieved by the enzyme as shown in FIG. 8. Under the stated conditions, there was an insignificant change in the erythrocyte mean corpuscular volume, mean corpuscular hemoglobin, and mean corpuscular hemoglobin concentration. Furthermore, there was little visible hemolysis. Morphologically, treated cells exhibited a mixed population of normocytes and spiculated cells as described by others (Goldstein et al., 1982). Incubation at 37° C. was necessary because dilute concentrations of glycosidase were used. Lower temperatures and shorter incubations achieved deantigenation, however, much higher enzyme concentrations are required.

Throughout this application, various publications are referenced. Full citations for the referenced not cited herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

Summary of Gallus N-acetyl-α-D-galactosaminidase purification[+]

| Step | Protein (mg) | Total Activity (μmoles/min) | Purification (fold) | Specific Activity (μmoles/ mg/min) | Yield (%) |
|---|---|---|---|---|---|
| 1 | 20,056.40 | 540.73 | 1.00 | 0.03 | 100.00 |
| 2 | 354.14 | 232.98 | 22.00 | 0.66 | 43.08 |
| 3 | 92.12 | 107.73 | 39.00 | 1.17 | 19.92 |
| 4 | 21.34 | 84.87 | 132.66 | 3.98 | 15.70 |
| 5 | 1.98 | 46.73 | 786.67 | 23.60 | 8.64 |
| 6 | 0.38 | 19.20 | 1,684.00 | 50.52 | 3.55 |

[+]Data is expressed as the mean value of three different preps.

TABLE II

Amino acid composition of Gallus N-acetyl-α-D-galactosaminidase.

| amino acid | residues* mole | amino acid | residues mole |
|---|---|---|---|
| ASP | 50 | MET | 16 |
| THR | 20 | ILE | 28 |
| SER | 26 | LEU | 45 |
| GLU | 45 | TYR | 18 |
| PRO | 28 | PHE | 17 |
| GLY | 43 | LYS | 17 |
| ALA | 37 | HIS | 4 |
| CYS | 10 | ARG | 30 |
| VAL | 22 | | |

*Residues per mole expressed in integer values.

TABLE III

Kinetic Parameters of Gallus N-acetyl-α-D-galactosaminidase.

| Substrate | Km* | Turnover Number[+] |
|---|---|---|
| ONP-N-acetyl-α-D-galactosaminide | 2.40 | 637 |
| PNP-N-acetyl-α-D-galactosaminide | 1.19 | 2370 |
| PNP-α-D-galactopyranoside | 10.69 | 201 |

*Data is expressed as the mean of six independent determinations
[+]Moles of substrate hydrolyzed per mole of enzyme per minute

TABLE IV

Substrate Specificity of Gallus N-acetyl-α-D-galactosaminidase.

| Substrate | Relative Activity # (%) |
|---|---|
| PNP-N-acetyl-α-D-galactosaminide | 100.00 |
| PNP-N-acetyl-β-D-galactosaminide | <0.08 |
| PNP-N-acetyl-α-D-glucosaminide | <0.08 |
| PNP-N-acetyl-β-D-glucosaminide | <0.08 |
| PNP-α-D-galactopyranoside | 12.74 |
| PNP-β-D-galactopyranoside | <0.08 |
| PNP-α-D-glucopyranoside | <0.08 |
| PNP-β-D-glucopyranoside | <0.08 |
| PNP-α-L-arabinopyranoside | <0.08 |
| PNP-α-L-fucopyranoside | <0.08 |
| PNP-β-L-fucopyranoside | <0.08 |
| 4-MU-α-D-galactopyranoside | 100.00 |
| 4-MU-N-acetyl-α-neuraminic acid | <0.01 |

Relative activity is expressed as % of enzyme activity on the corresponding conjugate.

TABLE V

Summary of α-N-acetyl-galactosaminidase improved purification[†]

| Step | Protein (mg) | Total Activity (μmoles/ min) | Yield (%) | Specific Activity (μmoles/ mg/min) | Purification (fold) |
|---|---|---|---|---|---|
| Crude Extract | 42,750.0 | 754.6 | 100.0 | 0.018 | 1.0 |
| Affinity Concentrate | 6.1 | 434.7 | 57.6 | 71.03 | 3946.0 |

[†]Data is expressed as the mean value from three different preps

TABLE VI

Substrate Specificity of Gallus-α-N-acetyl-galactosaminidase Improved Purification Scheme.

| Substrate | Relative Activity # (%) |
|---|---|
| PNP-N-acetyl-α-D-galactosaminide | 100.00 |
| PNP-N-acetyl-β-D-galactosaminide | <0.08 |
| PNP-N-acetyl-α-D-glucosaminide | <0.08 |
| PNP-N-acetyl-β-D-glucosaminide | <0.08 |
| PNP-α-D-galactopyranoside | 15.79 |
| PNP-β-D-galactopyranoside | <0.08 |
| PNP-α-D-glucopyranoside | <0.08 |
| PNP-β-D-glucopyranoside | <0.08 |
| PNP-α-L-arabinopyranoside | <0.08 |
| PNP-α-L-fucopyranoside | <0.08 |
| PNP-β-L-fucopyranoside | <0.08 |
| 4-MU-α-D-galactopyranoside | 100.00 |
| 4-MU-N-acetyl-α-neuraminic acid | <0.01 |

Relative activity is expressed as % of enzyme activity on the corresponding conjugate.

REFERENCE

Allen, "Sequencing of Proteins and Peptides", *Laboratory Techniques in Biochemistry and Molecular Biology*, pp. 95–99 and 252–253, Elsevier, Amsterdam (1989)

Bryant, "Antibody Identification and Titration", *An Intro. to Immunohematology*. (W. B. Saunders, Philadelphia) pp. 280–297 (1982)

Cregg et al, "Recent Advances in the Expression of Foreign Genes in *Pichia pastoris*", *Bio/Technology* 11:905–910 (1993).

Dahr, "Immunochemistry of Sialoglycoproteins in Human Red Blood Cell Membranes", in *Recent Advances in Blood Group Biochemistry*, American Assoc. Blood Banks, Arlington, Va., 23–50 (1986)

Dean et al., "Fabry Disease: α-Galactosidase A Deficiency", in *Practical Enzymology of the Sphingolipidoses*, Alan R. Liss, Inc., N.Y., (1977a)

Dean et al., "Identification of α-Galactosidase B from Human Liver as an α-N-Acetylgalactosaminidase", *Biochem. Biophys. Res. Commun.* 77:1411–1417 (1977b)

Dean et al., "Studies on Human Liver α-Galactosidases", *J. Biol. Chem.* 254:10001–10005 (1979)

Economidou et al., "Quantitative measurements concerning A and B antigen sites" *Vox Sang.* 12:321–328 (1967)

Feinberg & Goldstein, "A Technique for Radiolabeling DNA Restriction Endonucleases to High Specific Activity", *Anal Biochem* 132:6–12 (1983)

Fong et al., "Developmental patterns of ABO isoagglutinins in normal children correlated with the effects of age, sex, and maternal isoagglutinins" *Transfusion* 14:551–559 (1974)

Gilboa et al., "Transfer and expression of cloned genes using retroviral vectors" *BioTechniques* 4(6):504–512 (1986)

Goldstein et al., "Group B erythrocytes converted to group O survive normally in A, B, and O individuals" *Science* 215:168–170 (1982)

Goldstein, "Preparation of Transfusable Red Cells by Enzymatic Conversion", *The Red Cell*, 6th Ann Arbor Conf., 139–157 (1984)

Goldstein, "Conversion of ABO Blood Groups" *J. Trans. Med. Rev.* 3:206–212 (1989)

Harmening, "Evaluation of Panel Results" *Modern Blood Banking and Transfusion Practices*, F. A. Davis, Philadelphia, Pa., 212 (1989)

Harpaz et al., "α-Galactosidase", *Meth. Enzymol.*, 34:347–350 (1974)

Hata et al., "Purification and Characterization of N-Acetyl-α-D-Galactosaminidase", *Biochem Intl.* 28:77–89 (1992)

Henikoff, "Unidirectional digestion with exonuclease III creates targeted breakpoints for DNA sequencing", *Gene* 28:351–359 (1984)

Innis et al., "Degenerate Primers for DNA Amplification" *PCR Protocols*, a guide to methods and applications, Academic Press, San Diego, pp 45–55 (1990)

Issitt, "Biochemistry of the H, Lewis and Related Antigens", in *Applied Blood Group Serology* (Montgomery) Scientific Publications, Miami, Fla., 173–178, 194–196, and 209–214 (1985)

Itoh and Uda, "α-N-Acetylgalactosaminidase from Squid Liver: Purification and Characterization of Two Enzymes", *J. Biochem.* 95:959–970 (1984)

Kadowaki et al., "Isolation and Characterization of Blood Group A Substance-degrading-α-N-Acetylgalactosaminidase from an Acremonium sp.", *Agri. Biol. Chem.* 53:111–120 (1989)

Koide et al., "A case of Fabry's disease in a patient with no α-galactosidase A activity caused by a single amino acid substitution of Pro-40 by Ser", *FEBS Lett.* 259:353–356 (1990)

Kubo, "Changes in the specificity of blood groups induced by enzymes from soil fungi" *J. Forensic Sci.* 34:96–104 (1989)

Kusiak et al., "Purification and Properties of the Two Major Isozymes of α-Galactosidase from Human Placenta", *J. Biol. Chem.* 253:184–190 (1978)

Laemmli "Cleavage of structural proteins during the assembly of the head of bacteriophage T4" *Nature* 227:680–685 (1970)

Landsteiner, "Uber agglutination-serscheinungen normalen menschlichen blutes" *Klin. Wschr.* 14:1132 (1901)

Macfarlane et al.,"Contribution of microflora to proteolysis in the human large intestine", *J. Appl. Bacteriol.* 64:37–46 (1988)

Matsudaira, "Sequence from Picomole Quantities of Proteins Electroblotted onto Polyvinylidene Difluoride Membranes", *J. Biol. Chem.* 282:10,035–10,038 (1987)

McDonald et al., "α-N-Acetylgalactosa from *Aspergillus niger*", *Meth Enzymol* 28:735–738 (1972)

McGuire et al., "β-N-Acetylglucosaminidase, α-N-Acetylgalactos-aminidase and β-Galactosidase from Clostridium perfringens", *Meth Enzymol* 28:755–763 (1972)

Mollison, "ABO Lewis Ii and P Groups", in *Blood Transfusion in Clinical Medicine*, (Blackwell Scientific Publications, London) pp. 267–327 (1987)

Moore et al., "A modified ninhydrin reagent for the photometric determination of amino acids and related compounds", *J. Bio. Chem.* 211:907–913 (1954)

Nakagawa et al., "Purification and Characterization of α-N-Acetylgalactosaminidase from Skipjack Liver", *J. Biochem.*, 101:855–862 (1987)

Overbeek et al., "Cloning and Nucleotide Sequence of the α-Galaltosiotse cDNA from Cyamopsis Tetragonoluba (Guar) *Plant Mol. Biol.* 13:541–550 (1989)

Romano and Mollison, "Red cell destruction in vivo by low concentrations of IgG anti-A" *Br. J. Haematol* 29:121–127 (1987)

Sambrook et al., "Molecular cloning: A Laboratory Manual", 2nd Edition, pp 6.46–6.48, 8.46–8.51, Cold Spring Harbor Lab., Cold Spring Harbor (1989)

Sandhu et al., *Biotechniques* 12:14–16 (1992)

Schmidt, "The Mortality from Incompatible Transfusion", in *Immunobiology of the Erythrocyte* (Alan R. Liss Inc., New York) pp.251–261 (1980)

Schram et al., "The Identity of α-Galactosidase B from Human Liver", *Biochim Biophys.* Acta 482:138–144 (1977)

Smith et al., "Measurement of Protein Using Bicinchoninic Acid", *Anal. Biochem.*, 150:76–85 (1985)

Sumner-Smith et al., "Analysis of inducible MELI gene of Saccharomyces carlsbergensis and it secreted product, α-galactosidase (Melibase) *Gene* 36:333–340 (1985)

Sung and Sweeley., "Purification and Partial Characterization of Porcine Liver α-N-Acetylgalactosaminidase", *J. Biol. Chem.* 255:6589–6594 (1980)

Tsuji et al., "Molecular Cloning of a Full-Length cDNA for Human α-N-Acetylgalactosamidase (α-Galactosidase B)", *Biochem. Biophys. Res. Commun.* 163:1498–1509 (1989)

Twining, "Fluorescein Isothiocyanate-Labeled Casein Assay for Proteolytic Enzymes" *Anal. Biochem.* 143:30–34 (1984)

Uda et al., "α-N-Acetylgalactosaminidase from the Limpet, *Patella vulgata*", *J. Biol. Chem.* 252:5194–5200 (1977)

Uhlenbruck et al., *Allergie Klin. Immunol.* 138:423 (1969)

Walker, "Receptor-like protein kinase genes of *Arabidopsis thaliana*", *The Plant Journal* 3:451–456 (1993)

Wang et al., "Human α-N-Acetylgalactosaminidase-Molecular Cloning, Nucleotide Sequence, and Expression of a Full-length cDNA", *J. Biol. Chem.* 265:21859–21866 (1990)

Wantanabe et al., "Status of Blood Group Carbohydrate Chains in Ontogenesis and in Oncogenesis", *J.Exp. Med.* 144:644–653 (1976)

Weissmann, "α-Acetylgalactosaminidase from Beef Liver", *Meth. in Enzymol.* 28:801–805 (1972)

Weissmann et al, "Mammalian α-Acetylgalactosaminidase. Occurrence, Partial Purification, and Action on Linkages in Submaxillary Mucins", *Biochem.* 8:2034–2043 (1969)

---

What is claimed is:

1. A purified and isolated cDNA clone as set forth in SEQ ID No:1 encoding the mature chicken α-N-acetylgalactosaminidase enzyme.

2. A vector which comprises the DNA of claim 1.

3. A host cell, wherein the host cell is selected from the group of eucaryotic and procaryotic cells, which is transformed with the vector of claim 2.

4. The host cell of claim 3 wherein it is *E. coli*.

5. The host cell of claim 3 wherein it is *Pichia pastoris*.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2334 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: misc_feature
        ( B ) LOCATION: 2316..2334

( x i ) SEQUENCE DESCRIPTION: SEQ ID NO:1:

```
CTGGAGAACG GGCTGGCGCG GACCCCGCCC ATGGGCTGGT TGGCCTGGGA GCGGTTCCGC        60
TGCAACGTGA ACTGCCGGGA GGACCCCGC CAGTGCATCA GTGAGATGCT CTTCATGGAG       120
ATGGCAGACC GAATAGCAGA GGACGGCTGG AGGGAGCTGG GCTACAAGTA CATCAATATC      180
GATGACTGCT GGGCCGCCAA GCAGCGTGAC GCTGAGGGGC GGCTGGTGCC TGACCCCGAG      240
AGGTTCCCCC GGGGCATTAA GGCCTTGGCT GACTACGTTC ATGCCCGAGG CTTGAAGCTG      300
GACATTTATG GCGACCTGGG CAGACTCACC TGTGGAGGCT ACCCAGGCAC CACGCTGGAC      360
CGTGTGGAGC AGGACGCACA GACCTTCGCT GAGTGGGGTG TGGACATGCT GAAGCTAGAT      420
GGGTGCTACT CATCGGGGAA GGAGCAGGCA CAGGGCTACC ACAAATGGC AAGGGCCTTG       480
AACGCCACTG GCCGCCCCAT CGTCTACTCC TGCAGCTGGC CAGCCTACCA GGGGGGGCTG      540
CCTCCCAAGG TGAACTACAC TCTCCTGGGT GAGATCTGCA ACCTGTGGCG GAACTACGAT      600
GACATCCAGG ACTCATGGGA CAGCGTGCTT TCCATCGTGG ACTGGTTCTT CACAAACCAG      660
GATGTGCTGC AGCCGTTTGC TGGCCCTGGC CACTGGAATG ACCCAGACAT GCTCATCATT      720
GGAAATTTCG GTCTCAGCTA TGAGCAGTCA CGTTCCCAAA TGGCCTTGTG GACCATTATG      780
GCAGCTCCAC TCCTCATGTC CACCGACCTG CGCACTATCT CGCCGAGTGC CAAGAAGATT      840
CTGCAGAACC GCCTGATGAT CCAGATAAAC CAGGACCCCT TGGGAATCCA GGGGCGCAGG      900
ATCATCAAGG AGGGATCCCA CATTGAGGTG TTCCTGCGCC CGCTGTCACA GGCTGCCAGT      960
GCCCTGGTCT TCTTCAGCCG GAGGACAGAC ATGCCCTTCC GCTACACCAC CAGTCTGGCC     1020
AAGCTTGGCT TCCCCATGGG AGCTGCATAT GAGGTGCAAG ACGTGTACAG TGGGAAGATC     1080
ATCAGTGGCC TGAAGACAGG AGACAACTTC ACAGTGATCA TCAACCCCTC AGGGGTGGTG     1140
ATGTGGTACC TGTGTCCCAA AGCACTGCTC ATCCAGCAGC AAGCTCCTGG GGGGCCCTCA     1200
CGCCTGCCCC TTCTGTGAGC CCATGGCCAT TGGGAGCCCT GGGATACATC TCACCGCTGC     1260
TCAAGTGCCT TCTTCTGGTG TGGCTGGGGG AGGACATGCA GCTTGCTCCT CTGGACCACC     1320
TGATGATTTC TACTATTCCA CGTGAAGCAG GACTTCTTGT TACTCCCTCC TGAGAGCATG     1380
CAAAGCGCTC TGAGGTCCTC CTGTGGAAGA GGAGTGTTCC CAGTGACCAT TCTTTAGGAC     1440
```

```
CAGATGTGGT    CACCTTTTTT    CCTTTGCTTG    GCTTAGGACA    AAGGGCTGTC    CACAGGGCTG    1500

CACCCCTCTT    CCCAGGCACC    ATCCCCAGAC    CAGGAGCTCC    TGGGGCCAGG    CTGTCTCTGT    1560

CTGGCAGGCA    GGATCAGCAG    GTAACACCAC    TACAGTGTAG    TCGCACATAA    TGAAAAAGAA    1620

ATCTAAACAA    AACGTGTGCC    AGTAGTGTAC    TGAACCCGCT    CTGGTTACAG    CAGAGCAAAA    1680

CCTGAGTTGT    CCATGCACAA    TCCCGTATCC    TCACTGTGGT    GTTAGCATGA    AAAATTGCAG    1740

TCACAGTGCA    TTGTGCACGA    GTGGTGTCTG    GAAGATGCTG    ATGCTTGTTC    GTGGTGGTCT    1800

TAAGGTGGGA    GATGCTCATG    GGTGCTGGCC    AAGTTGCATC    TCAATCTTGT    GAGGCTGAAC    1860

CTTCCAGCAT    TTCTCAGGGA    AAGGCTCTTC    CTTTTAAGGC    AGCCTGCACA    AATAGAAGGG    1920

GCTCAGAAGG    AGCCACGGAG    GAGGGGCTCA    GGTGGGCCGT    GGCCTCCCCT    GACCACCCCA    1980

AGAGGGGTGC    AACACTCACC    AAAATCACCC    CTTCCAAGGC    CAGGGCAGCC    CAGGGAGACG    2040

CACCCAAGGT    TAACCTCAAA    ACAGGAAATC    ACCCTATTTT    AAATTAGTGA    GAAATTGAAC    2100

TTCCCCATTC    TATCAGATGA    GGGCTAGAAG    CCACTCTCCT    TAGAAGGCCA    CGTGGCGGAT    2160

TCCTGCCCCT    TGCAGAGACA    TTGTGGTGCT    GAAGCAAGAT    GCTGATGTGA    TGCTTTGCAG    2220

CGCTGGAAAT    GACATGTCTG    TTTCATGCTT    GTGTGGGAGC    TGGCTTTGTT    TTTGTGATTT    2280

TGACAATTTA    ACTGAAATAA    AAGGGAAGCA    GAGGGAAAAA    AAAAAAAAA     AAAA          2334
```

( 2 ) INFORMATION FOR SEQ ID NO:2:

( i ) SEQUENCE CHARACTERISTICS:
        ( A ) LENGTH: 405 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:2:

```
Leu  Glu  Asn  Gly  Leu  Ala  Arg  Thr  Pro  Pro  Met  Gly  Trp  Leu  Ala  Trp
 1              5                        10                       15

Glu  Arg  Phe  Arg  Cys  Asn  Val  Asn  Cys  Arg  Glu  Asp  Pro  Arg  Gln  Cys
           20                       25                       30

Ile  Ser  Glu  Met  Leu  Phe  Met  Glu  Met  Ala  Asp  Arg  Ile  Ala  Glu  Asp
           35                       40                       45

Gly  Trp  Arg  Glu  Leu  Gly  Tyr  Lys  Tyr  Ile  Asn  Ile  Asp  Asp  Cys  Trp
      50                  55                       60

Ala  Ala  Lys  Gln  Arg  Asp  Ala  Glu  Gly  Arg  Leu  Val  Pro  Asp  Pro  Glu
 65                      70                       75                       80

Arg  Phe  Pro  Arg  Gly  Ile  Lys  Ala  Leu  Ala  Asp  Tyr  Val  His  Ala  Arg
                85                       90                       95

Gly  Leu  Lys  Leu  Asp  Ile  Tyr  Gly  Asp  Leu  Gly  Arg  Leu  Thr  Cys  Gly
               100                      105                      110

Gly  Tyr  Pro  Gly  Thr  Thr  Leu  Asp  Arg  Val  Glu  Gln  Asp  Ala  Gln  Thr
           115                      120                      125

Phe  Ala  Glu  Trp  Gly  Val  Asp  Met  Leu  Lys  Leu  Asp  Gly  Cys  Tyr  Ser
      130                      135                      140

Ser  Gly  Lys  Glu  Gln  Ala  Gln  Gly  Tyr  Pro  Gln  Met  Ala  Arg  Ala  Leu
145                      150                      155                      160

Asn  Ala  Thr  Gly  Arg  Pro  Ile  Val  Tyr  Ser  Cys  Ser  Trp  Pro  Ala  Tyr
                165                      170                      175

Gln  Gly  Gly  Leu  Pro  Pro  Lys  Val  Asn  Tyr  Thr  Leu  Leu  Gly  Glu  Ile
                180                      185                      190
```

|       |     |     |     |     |     |     |     |     |     |     |     |     |     |     |
|-------|-----|-----|-----|-----|-----|-----|-----|-----|-----|-----|-----|-----|-----|-----|
| Cys | Asn | Leu 195 | Trp | Arg | Asn | Tyr | Asp 200 | Asp | Ile | Gln | Asp 205 | Ser | Trp | Asp | Ser |
| Val | Leu 210 | Ser | Ile | Val | Asp 215 | Trp | Phe | Phe | Thr | Asn 220 | Gln | Asp | Val | Leu | Gln |
| Pro 225 | Phe | Ala | Gly | Pro 230 | Gly | His | Trp | Asn | Asp 235 | Pro | Asp | Met | Leu | Ile | Ile 240 |
| Gly | Asn | Phe | Gly | Leu 245 | Ser | Tyr | Glu | Gln 250 | Ser | Arg | Ser | Gln | Met 255 | Ala | Leu |
| Trp | Thr | Ile | Met 260 | Ala | Ala | Pro | Leu 265 | Leu | Met | Ser | Thr | Asp 270 | Leu | Arg | Thr |
| Ile | Ser | Pro 275 | Ser | Ala | Lys | Lys | Ile 280 | Leu | Gln | Asn | Arg | Leu 285 | Met | Ile | Gln |
| Ile | Asn 290 | Gln | Asp | Pro | Leu | Gly 295 | Ile | Gln | Gly | Arg | Arg 300 | Ile | Ile | Lys | Glu |
| Gly 305 | Ser | His | Ile | Glu | Val 310 | Phe | Leu | Arg | Pro | Leu 315 | Ser | Gln | Ala | Ala | Ser 320 |
| Ala | Leu | Val | Phe | Phe 325 | Ser | Arg | Arg | Thr | Asp 330 | Met | Pro | Phe | Arg | Tyr 335 | Thr |
| Thr | Ser | Leu | Ala 340 | Lys | Leu | Gly | Phe | Pro 345 | Met | Gly | Ala | Ala | Tyr 350 | Glu | Val |
| Gln | Asp | Val 355 | Tyr | Ser | Gly | Lys | Ile 360 | Ile | Ser | Gly | Leu | Lys 365 | Thr | Gly | Asp |
| Asn | Phe 370 | Thr | Val | Ile | Ile | Asn 375 | Pro | Ser | Gly | Val | Val 380 | Met | Trp | Tyr | Leu |
| Cys 385 | Pro | Lys | Ala | Leu | Leu 390 | Ile | Gln | Gln | Gln | Ala 395 | Pro | Gly | Gly | Pro | Ser 400 |
| Arg | Leu | Pro | Leu | Leu 405 |

( 2 ) INFORMATION FOR SEQ ID NO:3:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

GCGGATCCGA TGCTCAGACC TTCGCCGAGT GGAAGGTAGA CATGCTCAAG CTGGATGGC    59

( 2 ) INFORMATION FOR SEQ ID NO:4:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

ATTCAGGGCA GCAGCCATCT TGGGGTACCC CTGGGCCCGC TCCTCGGGGG TGGAGAAGCA    60

GCCATCCAGC TTGAG    75

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

```
GCTGCTGCCC TGAATGCCAC AGGCCGCCCC ATCGCCTTCT CCTGC                    45
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (xi) SEQUENCE DESCRIPTION: SEQ ID NO:6:

```
GCGAATTCGC AGGAGAAGGC GAT                                            23
```